United States Patent [19]
Edwards

[11] Patent Number: 4,954,130
[45] Date of Patent: Sep. 4, 1990

[54] CATHETER/HEPARIN LOCK AND METHOD OF USING SAME

[75] Inventor: John Edwards, Orange, Calif.

[73] Assignee: William P. Waters, Balboa Island, Calif.

[21] Appl. No.: 341,701

[22] Filed: Apr. 17, 1989

Related U.S. Application Data

[63] Continuation of Ser. No. 146,267, Jan. 20, 1988, abandoned.

[51] Int. Cl.⁵ .............................................. A61M 5/178
[52] U.S. Cl. ...................................... 604/169; 604/248
[58] Field of Search ............... 604/169, 167, 164, 248, 604/244, 245, 246, 256, 247

[56] References Cited

U.S. PATENT DOCUMENTS

| | | | |
|---|---|---|---|
| 1,089,805 | 3/1914 | Wolf | 604/169 |
| 3,057,350 | 10/1962 | Cowley | 604/248 |
| 3,895,632 | 7/1975 | Plowieck | 604/169 |
| 4,106,491 | 8/1978 | Guerra | 604/169 |
| 4,126,133 | 11/1978 | Schwartz | 604/169 |
| 4,230,128 | 10/1980 | Aramayo | 604/248 |
| 4,447,235 | 5/1984 | Clarke | 604/169 |
| 4,540,411 | 9/1985 | Bodicky | 604/169 |
| 4,585,440 | 4/1986 | Tcheruenkov et al. | 604/167 |
| 4,689,047 | 8/1987 | Bauer | 604/169 |

FOREIGN PATENT DOCUMENTS 575559 8/1924 France .................. 604/169

Primary Examiner—Stephen C. Pellegrino
Assistant Examiner—Kathleen A. Daley
Attorney, Agent, or Firm—Bernard L. Kleinke; William Patrick Waters; Jerry R. Potts

[57] ABSTRACT

An improved intravenous catheter/heparin lock combination having a tip, a body, an IV port and a movable hollow plug; the exterior of the plug having a self-sealing membrane through which needles may be inserted. The plug is movable within the body so as to function as a valve in relation to fluid flow through the port.

A method of using the combination wherein the plug may be positioned to control fluid flow through the port and medications may be administered by needle through the plug independently of fluid flow through the port.

5 Claims, 1 Drawing Sheet

CATHETER/HEPARIN LOCK AND METHOD OF USING SAME

This is a Continuation, of application Ser. No. 07/146,267, filed on 1-20-88 now abandoned.

BACKGROUND OF THE PRESENT INVENTION

The present invention relates to an intravenous catheter lock combination and more particularly to an improved catheter/heparin lock combination and the method of its use.

It is frequently necessary in a hospital or emergency setting for a physician, nurse, paramedic or other professional attending a patient to administer fluids to the patient. This is often accomplished by catheterizing the patient through the isertion of a catheter, or tube, into one of the patient's veins. In general, the insertion of the catheter occurs in a vein in one of the patient's extremities.

At the present time, the technique of catheterization is accomplished, first, by the introduction into the patient's vein of a needle enclosing which, in sleeve-like fashion, is an intravenous catheter. The needle penetrates the wall of the vein and as it is inserted into the lumen of the vein, the catheter follows. With the catheter thereby introduced into the vein, the needle is removed. Prior to needle removal, it is common practice to draw a small quantity of blood into the needle in order to verify that the vein has been entered. At this point, both catheter and needle contain blood from the patient.

Immediately prior to the time the needle is removed, pressure is applied to the vein at a point distal to the catheter/needle insertion point in order to prevent the extravasation of blood from the catheter.

As a general rule, at this point the catheter is connected to a fluid source such as a saline bag by intravenous tubing ("IV tubing"). In the present art, intermediate the fluid source and the catheter one or more IV ports are located. These ports are usually chambers located against, parallel to and in communication with the IV tubing and which are capped at their outer end by a rubber-like, resealable membrane. The ports are utilized for the administration of medicines and drugs into the fluid stream while the patient is still connected to the fluid source. Such utilization is seen, for example, in the treatment of hemophiliacs when it is necessary to administer Factor 8 concentrate, an intravenous medication to enchance blood clotting. In practice, the technique commonly employed is to clamp the IV tubing and inject the medication through an IV port. After injection of the medication into the fluid stream, the needle is removed from the IV port and leak tight integrity is maintained by virtue of the resealable membrane. In other cases, such as those where the patient is diabetic and in ketoacidosis, insulin may be introduced into the IV fluid stream through an IV port.

As is illustrated by the above examples, the IV ports provide flexibility but require continued hookup of the patient to the IV bag. At present, when the patient has attained satisfactory fluid balance and the need continues for access to the patient's vein for administration of medication, a conversion to a heparin lock is effected. The term "heparin lock" denotes an apparatus, indwelling the patient's vein for a period of time and utilized for the introduction of medication into the patient's vein. The heparin lock is flushed from time to time with heparin in order to prevent coagulation of blood in the lock.

The conventional method for accomplishing conversion from hookup to the IV bag to the heparin lock requires the performance of the following steps: (1) removal of the intravenous tubing from the end of the catheter, that is at the end proximal to the insertion point of the catheter into the patient's vein, (2) applying pressure distal to the catheter insertion point to prevent blood from escaping from the now open end of the catheter, (3) the procurement of a heparin lock from its sterile container and (4) the insertion of the heparin lock into the catheter.

A disadvantage of this procedure is the cost involved since two sterile packs must be utilized. The first of such packs is comprised of the needle and the tubing connecting the patient to the fluid source. The second is the heparin lock itself. A second, and more serious, disadvantage is extravasation from the open catheter can easily occur with potential contamination of an operating theatre, for example, and of the medical staff itself. While this consideration has been one historically of concern to the medical staff when a patient with an infectious disease is treated, the presence of the AIDS virus in the body of some patients now makes the potential for medical staff contamination a life threatening event.

As more fully discussed below, the present invention comprises an IV catheter/heparin lock combination which reduces the conversion process to a one step procedure which is more economical than current methods, which presents a more easily performed procedure and which significantly reduces the potential for medical staff contamination by significantly reducing the potential for medical staff contamination by a patient's blood. In addition, the present invention provides the advantage of regulating the flow of IV fluids close to the point of entry into the patient's vein rather than, as presently seen, at the fluid source.

OBJECTS AND SUMMARY OF THE PRESENT INVENTION

It is an object of the present invention to provide a safe and versatile IV catheter/heparin lock.

It is a further object of the present invention to provide a more efficient and more economical IV catheter/heparin lock.

It is a still further object of the present invention to provide an IV catheter/heparin lock which eliminates the need for two sterile packs in certain medical functions.

The present invention specifically addresses and alleviates the above referenced deficiencies found in the art and comprises an improved IV catheter/heparin combination which is more efficient and safer in its function and which is more economical in use since it eliminates the necessity of a second sterile pack in many circumstances.

More particularly, in its preferred embodiment, the present invention comprises an IV catheter having at its proximal end a cylindrical body. Through an IV port in the body, appropriate fluids are administered to the patient.

Within the catheter body is a hollow, movable plug in leak tight relationship to the body. In a preferred embodiment, the plug is rotatable within the body and it contains an opening or cutout so that when the plug is rotated it acts as a valve opening or closing the port.

The plug extends beyond the body and it is readily apparent to one skilled in the art that the plug can be marked or indexed in such a manner as to provide a visual and a tactile indication of the relationship between the port and the opening or cutout in the plug. The plug has a resealable membrane at its outside end through which needles may be introduced.

BRIEF DESCRIPTION OF THE DRAWINGS

The accompanying drawings show, for purposes of exemplification and without limiting the invention or the claims to said invention, certain practical embodiment which illustrate the principles of this invention wherein:

DETAILED DESCRIPTION OF PREFERRED EMBODIMENT

Figure 1:
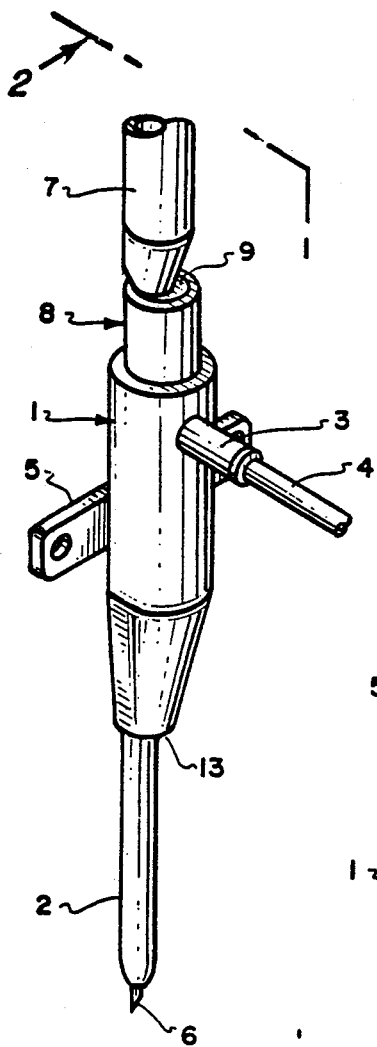
FIG. 1 is a plan view of the present invention depicting a needle inserted through the invention.

Referring to FIG. 1, and, for illustrative purposes only and not by way of limitation of the invention and its various applications, a preferred embodiment of the present invention is depicted. A cylindrical catheter body 1 terminates in tip 2 at one end. In use, tip 2 is inserted into the vein of a patient up to hub 13. At the end of catheter body 1 opposite tip 2 is plug 8 which is hollow and is sealed on its exposed end by self-sealing membrane 9. A typical hypodermic needle body 7 is depicted in contact with self-sealing membrane 9 while the tip of needle 6 is depicted as emerging through tip 2.

With further reference to FIG. 1, intravenous tubing (IV tubing) 4 is depicted as engaging IV port 3 which connects to catheter body 1. Opposite IV port 3 is flange 5.

In a typical application, tip 2 of the invention is inserted into the patient's vein up to hub 13 and the apparatus is taped to the body, typically an arm or leg, of the patient at flange 5. Fluid administration is initiated when the fluid source is connected by the insertion of IV tubing 4 into IV port 3. As will be more fully discussed below, flow of fluids through IV port 3 and into catheter body 1 occurs when IV port 3 is open. The pressure of the IV fluid is greater than venous pressure and, as a result, fluid flows into the vein through catheter body 1 and tip 2. Self sealing membrane 9 prevents fluid flow in the opposite direction.

At any time while the invention is in place, medications may be administered directly to the vein of the patient by the insertion of needle 6 through self sealing membrane 9. This can be accomplished either when fluid is at full flow through IV port 3 or when fluid flow through the port has been reduced or stopped. Upon removal of the needle, self-sealing membrane 9 prevents any leakage of fluid from plug 8.

It will be clear to one skilled in the art of inventions such as the one herein disclosed that it may be fabricated of metal such as stainless steel, or in a preferred embodiment, of transparent polyvinyl or other low cost, plastic-like material. Self-sealing membrane 9 is typically composed of one of several commercially available self-sealing rubber like materials.

Figure 2:
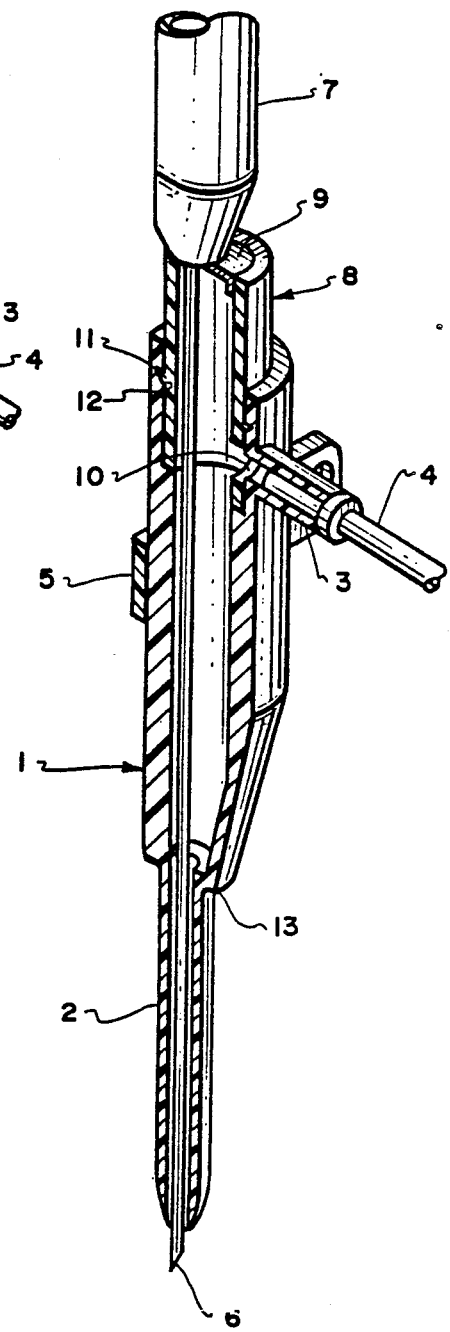
FIG. 2 is a view of the invention taken along the line 2—2 of FIG. 1.

In FIG. 2, catheter body 1, tip 2, IV port 3, plug 8, self-sealing membrane 9 and flange 5 are depicted in section. The relationship wherein IV tubing 4 is inserted into IV port 3 is also depicted as is the relationship of the invention to needle body 7 and needle 6.

Plug 8 is depicted in FIG. 2 as having an annular shoulder 11 which engages annular groove 12 in catheter body 1 so that plug 8 is securely and rotatably held within catheter body 1. As further depicted in FIG. 8, plug 8 is hollow and contains aperture 10 which is illustrated in a position whereby fluids are allowed to pass from IV port 3 into catheter body 1.

Figure 3:
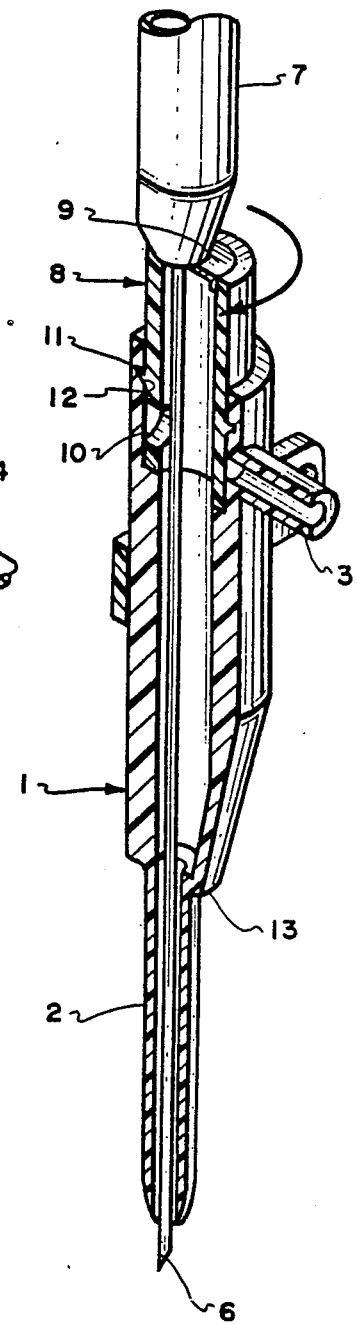
FIG. 3 is a lengthwise sectional view in which the plug has been rotated 180 degrees from its position in FIG. 2.

In FIG. 3, plug 8 is depicted as rotated 180 degrees from its position in FIG. 2. In this condition, aperture 10 has been rotated away from IV port 3 and fluids are thus prevented from entering catheter body 1. In this condition, the administration of IV fluids to the patient is stopped and IV tubing 4 may be disconnected. This step is by no means irreversible since fluid administration may be recommenced by attacment to the fluid source through IV tubing 4 and rotation of plug 8 until aperture 10 is aligned with IV port 3. It will be readily apparent to one skilled in the art that administration of medication through the self-sealing membrane may occur at any time independently of the relation of aperture 10 to IV port 3.

Figure 4:
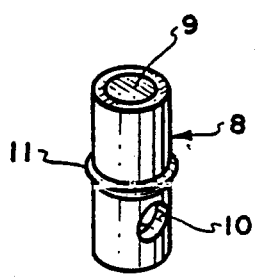
FIG. 4 is a plan view of the plug.

In FIG. 4, the relationships among self-sealing membrane 9, aperture 10 and annular shoulder 11 are depicted. It is readily apparent that plug 8 may be color coded or marked in such a manner as to provide a visual indication of its position in regard to IV port 3 and, further, may have index marks so that such relationship could be tactilly determined.

While the preferred embodiment is depicted as essentially cylindrical in cross section, it will be readily apparent to one skilled in the art of such inventions that cathether body 1 and plug 8 could be square or rectangular or otherwise shaped in cross section and still function within the contemplation of this disclosure. It will also be readily apparent that a cut away portion of plug 8 would allow a similar valving action as that performed by aperture 10 and further, that the valving action may be accomplished by means other than by rotation of plug 8 within cathether body 1. This could be accomplished, for example, by altering the relationship between IV port 3 and aperture 10 by sliding plug 8 within catheter body 1 rather than by rotating it. In addition, while one IV port is depicted as the preferred embodiment, it is clear that the invention would function with a plurality of IV ports and, with proper location of apertures in plug 8 could be designed to function with a plurality of IV ports simultaneously open or closed or in combination wherein one or more port would be open while one or more ports would be closed.

I claim:

1. An intravenous access device comprising:
    an elongated body having a hollow interior for the passage therethrough of fluid, said body having front and rear ends and having a hollow tip at the front end thereof for insertion into a vein;
    an intravenous fluid port connected to said body intermediate its ends for connection in fluid communication with a supply line connected in fluid communication with a source of intravenous fluid under pressure for delivering said fluid to the interior of said body for administration to a patient;

means disposed at said port for connecting sealably and removably the end of said line to said port;
a hollow tubular member disposed coaxially within said body located at the rear end thereof, said hollow member having a front and a rear opening;
a membrane closing said rear opening resealably for admitting injectable fluids therethrough;
means defining an aperture in the side of said member for being positioned in alignment with said port to permit said intravenous fluid to flow into the hollow interior of said body and for being positioned out of alignment with said port for fluid blocking purposes; and
means for mounting said member movably coaxially within said body for movement into and out of alignment with said intravenous fluid port to control fluid flow therethrough, so that said port can be closed and the supply line removed from said port, to permit said device to remain indwelling a vein and permitting introduction of injectable fluids through said membrane and the withdrawal of blood therethrough.

2. A device as recited in claim 1, having means for displaying the relationship between said hollow tubular member and said port.

3. A device as recited in claim 1, wherein said hollow tubular member is rotatably connected to said body.

4. A device as recited in claim 1, wherein said hollow tubular member is slidably connected to said body.

5. A method of using an intravenous access device having an elongated body having a hollow interior for the passage therethrough of fluid, said body having front and rear ends and having a hollow tip at the front end thereof for insertion into a vein; an intravenous fluid port connected to said body intermediate its ends for connection in fluid communication with a supply line connected in fluid communication with a source of intravenous fluid under pressure for delivering said fluid to the interior of said body for administration to a patient; means disposed at said port for connecting sealably and removably the end of said line to said port; a hollow tubular member disposed coaxially within said body located at the rear end thereof, said hollow member having a front and a rear opening; a membrane closing said rear opening resealably for admitting injectable fluids therethrough; means defining an aperture in the side of said member for being positioned in alignment with said port to permit said intravenous fluid to flow into the hollow interior of said body and for being positioned out of alignment with said port for fluid blocking purposes; and means for mounting said member movably coaxially within said body for movement into and out of alignment with said intravenous fluid port to control fluid flow therethrough, so that said port can be closed and the supply line removed from said port, to permit said device to remain indwelling a vein and permitting introduction of injectable fluids through said membrane and the withdrawal of blood therethrough; comprising the steps of:
  using syringes, each having a needle;
  inserting syringe needle through said membrane;
  inserting, into the vein of a person, the tip of said syringe needle and the tip of said device;
  withdrawing said syringe needle from the device;
  connecting said port to a source of intravenous fluid under pressure to deliver an intravenous fluid to the vein;
  positioning said aperture defining means in alignment with said port to permit said intravenous fluid to flow into the hollow interior of said body;
  permitting a predetermined volume of fluid to flow into said hollow interior;
  moving said hollow member to a fluid blocking position;
  removing the end of the line from said connecting means to enable said device to remain indwelling a vein for long periods of time; and
  subsequently inserting a syringe needle through said membrane to transfer fluids therethrough.

* * * * *